US005484385A

United States Patent [19]
Rishton

[11] Patent Number: 5,484,385
[45] Date of Patent: Jan. 16, 1996

[54] INTRA-AORTIC BALLOON CATHETER

[75] Inventor: Michael L. Rishton, Reading, Mass.

[73] Assignee: C. R. Bard, Inc., Murray Hill, N.J.

[21] Appl. No.: 230,832

[22] Filed: Apr. 21, 1994

[51] Int. Cl.$^6$ .................................................. A61B 19/00
[52] U.S. Cl. .................................. 600/16; 623/3; 606/19
[58] Field of Search ........................ 600/16, 18; 606/191, 606/192, 194; 604/96, 103; 623/3

[56] References Cited

U.S. PATENT DOCUMENTS

| | | |
|---|---|---|
| 726,009 | 4/1903 | Whisler . |
| 3,504,662 | 5/1967 | Jones . |
| 3,585,983 | 6/1971 | Kantrowitz . |
| 3,720,199 | 3/1973 | Rishton et al. . |
| 4,051,840 | 10/1977 | Kantrowitz et al. . |
| 4,311,133 | 1/1982 | Robinson . |
| 4,351,341 | 9/1982 | Goldberg et al. . |
| 4,456,000 | 6/1984 | Schjeldahl et al. . |
| 4,470,218 | 9/1984 | Yu . |
| 4,850,348 | 7/1989 | Pell et al. . |
| 4,902,272 | 2/1990 | Milder et al. . |
| 4,902,273 | 2/1990 | Choy et al. . |
| 5,295,994 | 3/1994 | Bonutti ................................ 606/192 |
| 5,338,298 | 8/1994 | McIntyre .............................. 606/194 |
| 5,358,486 | 10/1994 | Saab ..................................... 604/96 |
| 5,383,856 | 1/1995 | Bersin ................................... 604/96 |
| 5,395,333 | 3/1995 | Brill ...................................... 604/96 |

OTHER PUBLICATIONS

Various literature references found as a result of database searches (see attached sheet for complete listing).
"Rupture of the Intra–aortic Balloon," pp. 4 and 5, with list of source publications and articles, pp. 11–14.
"Balloon Rupture," IABP Literature Search on Balloon Rupture, with list of references, pp. 5–8.
"Intraaortic Balloon Rupture," Kenneth D. Stahl et al, pp. 496–499, vol. XXXIV Trans Am. Soc. Artif. Intern Organs., 1988, pp. 496–499.
"The Tokai Medical Products Balloon: A Safe and Highly Durable New Balloon for the Intraaortic Balloon Pump," Hiroshi Nishida MD et al, vol. 1, No. 2, Asian Cardiovascular & Thoracic Annuals, Jun. 1993, pp. 110–112.
"Intraaortic Balloon Entrapment," Michael D. Horowitz, MD et al, Case Report, Ann. Thorac. Surg., 1993:56 pp. 368–370.
Confidential, Corp. Review Final Draft, IABP 510K, Jul. 30, 1992, pp. 185–186.
"Events Associated with Rupture of Intra–aortic Balloon Counterpulsation Devices," Francis P. Sutter et al, ASAIO TRANSACTIONS, vol. 37, No. 1, Jan. 1991, pp. 38–40.
Diseases of the Aorta, Joseph Lindsay, Jr., Lea & Bebinger, 1994, pp. 1–5.
Comprehensive Intraaortic Balloon Counterpulsation, Susan J. Quaal, Ph.D., Second Edition, Mosby, pp. 116, 113, 155, 163–164.
Arterial Function in Health and Disease, Michael F. O'Rourke, M.D., Churchill Livingstone, 1982, pp. 225–232.
"Ruptures of Intra–Aortic Balloonpump Catheters," by P. M. M. J. Rutten and N. G. Meijne, Presented at the 4th European Congress on Extra–corporeal Circulation Technology, 14 Jun. 1991.

Primary Examiner—William E. Kamm
Assistant Examiner—Marianne Parker
Attorney, Agent, or Firm—Dennison, Meserole, Pollack & Scheiner

[57] ABSTRACT

A balloon for an inter aortic balloon pump having an elongate tapered section extending from a proximal end of minimal diameter and progressively increasing in diameter toward the distal end. The tapered section is of greater wall thickness with the wall thickness becoming progressively thinner toward the distal end.

20 Claims, 1 Drawing Sheet

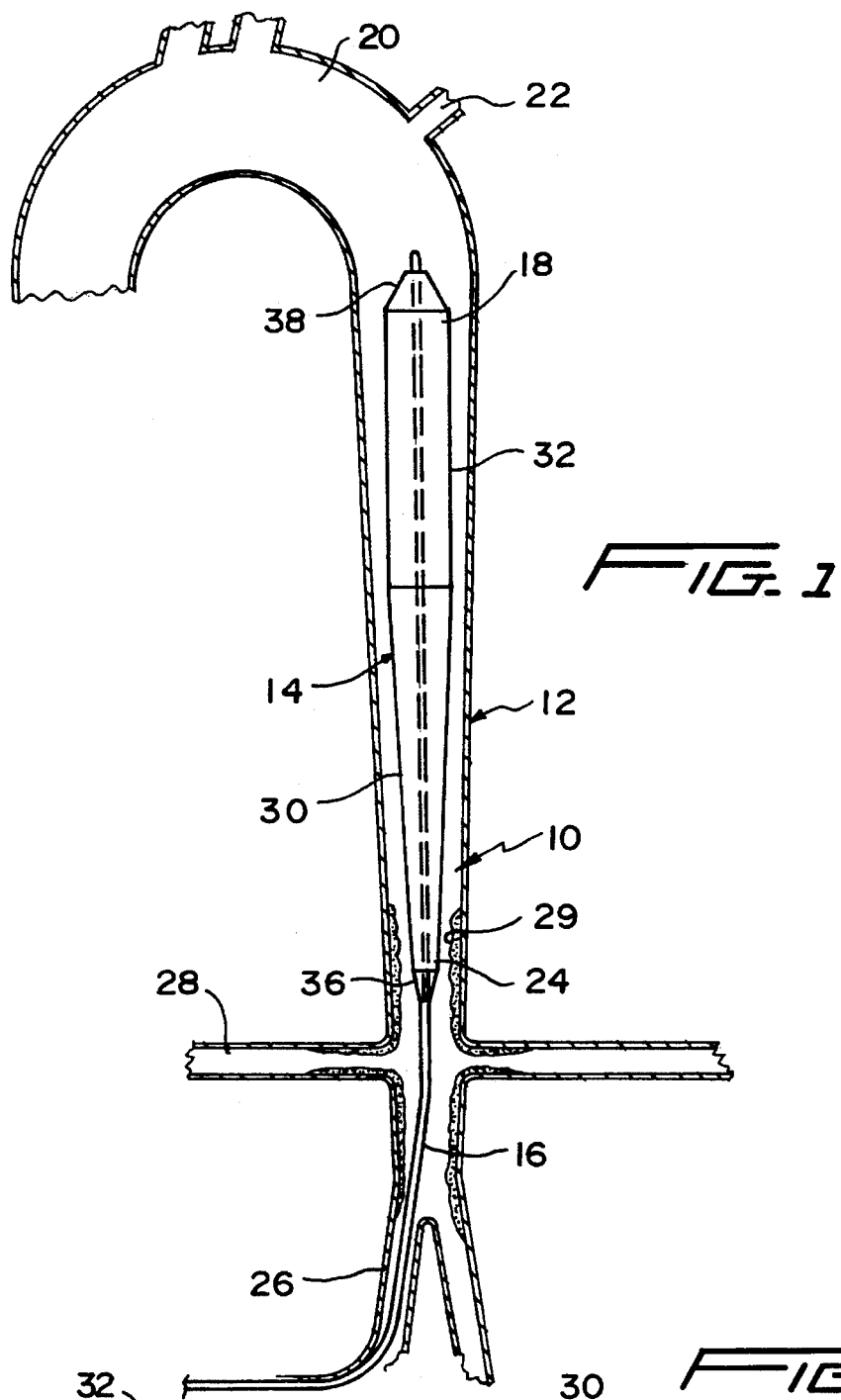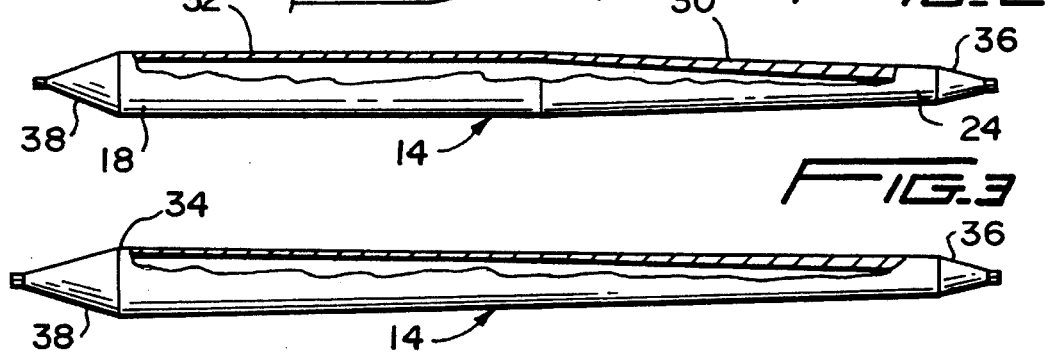

INTRA-AORTIC BALLOON CATHETER

BACKGROUND OF THE INVENTION

The intra-aortic balloon pump is a cardiac assist device which operates on the counterpulsation principal. The purpose of the device is to temporarily assist the pumping function of a diseased or damaged heart. The device consists of a catheter with a long narrow balloon attached toward the distal end thereof for insertion through a femoral artery into the descending aorta. The proximal end of the catheter is connected to an external control system which provides timing and volume control for inflation and deflation of the balloon with helium gas. Following its initial acceptance circa 1970, the balloon catheter has become an important adjunct in the treatment of cardiac failure resulting from myocardial infarction or surgical intervention.

In operation, the intra-aortic balloon assists the blood pumping function of the heart with the timed inflation and deflation of the implanted balloon. The balloon is inflated as the heart completes its blood ejection cycle, resulting in an increased aortic blood pressure and systemic blood flow due to the displaced volume of the inflated balloon. Immediately prior to the next ejection cycle, the balloon is deflated and aortic blood pressure falls, reducing the workload on the heart during ejection.

Since its initial introduction, the design and construction of the balloon catheter has seen many changes and several manufacturers have developed products for the market. One dramatic change in the design and application of the balloon catheter eliminated the need for a surgical cut down to the femoral artery for insertion and made possible the insertion of the balloon through a percutaneous insertion device. For this insertion technique, the balloon is wrapped or folded into the smallest possible size or cross section and inserted into the femoral artery through a tubular system called a sheath/dilator assembly. The new percutaneous insertion technique allows insertion of the balloon in a broader range of medical situations and by a larger physician group. There is nearly universal acceptance of this important new technique. The new design and technique, however, is not totally problem free and balloon leaks in particular have been a point of concern among user physicians.

In operation, the intra-aortic balloon is inflated and deflated with helium gas during each cycle of the heart, representing many thousands of cycles during the average patient application. Rupture of the balloon membrane, causing gas leakage into the blood stream or blood leakage into the balloon system can have disastrous results and must be avoided. Balloon membrane reliability is a key element in all balloon designs and balloon rupture was in initial balloon designs an extremely rare occurrence. However, the recent incidence of balloon rupture has been reported by some users to be as high as five percent and has become a matter of significant concern. It is also recognized that this increased incidence of balloon rupture is connected with the change from surgically implanted balloons to percutaneously inserted balloons.

A review of balloon rupture going back to the beginnings of balloon pump use shows that balloon rupture, although rare, was seen in all balloon designs. When these early ruptured balloons were examined in the laboratory the rupture was determined to be the result of abrasion. The examination of recent balloons has shown the same characteristic abrasions and are believed to be the result of contact with calcified vascular lesions in the region of the renal arteries and bifurcation of the femoral arteries. The presence of calcified atherosclerosis in the aorta is well known and attributed to arterial stresses acting over long periods of time. It is also known that these vascular lesions occur first in the areas of highest stress, including the lower aorta around the origin of major vessels. Evidence of abrasion on intra-aortic balloons, removed from patients, is also found predominantly in the proximal portion of the balloon that had been positioned in the lower aorta.

The increased incidence of balloon rupture is thought to be the result of two conditions. First, balloons designed for percutaneous insertion have approximately half the wall or membrane thickness of the originals designed for surgical insertion. Second, the average age of the balloon pump patient population has increased and calcification in the lower aorta is more common and extensive.

The common intra-aortic balloon, when inflated, has a long cylindrical membrane shape with the maximum allowable length of the balloon being restricted by the need to avoid obstruction of the left subclavian artery and the renal arteries. The conservative establishment of this length is based on physiologic measurements in a broad patient population and any extension of the balloon length could result in obstruction of major arteries.

As the common shape of intra-aortic balloons currently marketed are cylindrical and are of constant diameter and wall thickness over the entire length, and since the length of the balloon is fixed, the displacement volume of the balloon is required for a 40 c.c. displacement, the most common balloon size, is approximately 0.57 inches. This diameter is close to the diameter of the aorta in the region of the renal arteries and brings the balloon wall within close proximity to the aorta wall. A protrusion of calcified atherosclerotic plaques can therefore come in nearly constant contact with the balloon during the inflation cycle.

A patent to R. T. Jones, U.S. Pat. No. 3,504,662, issued Apr. 7, 1970, very early in the development of intra-aortic balloon pumps and prior to development of the percutaneous insertion technique now practically universally accepted, broadly refers to varying the diameter of a compartmented membrane along the length thereof to provide a tapered configuration for the stated purpose of fitting within the aorta. The problem of abrasion-induced rupture was not recognized in Jones, and in fact did not appear until substantially later as a result of the development of the percutaneous insertion technique which required substantially thinner wall thicknesses for the membrane. This in turn led to an increase in the incidence of rupture and ultimately an extensive investigation into the causes thereof. The major factor in membrane rupture was found to be abrasion resulting from the presence of calcified atherosclerosis coupled with the thinner wall or membrane thickness required for percutaneous insertion.

Balloons of the type originally used in conjunction with femoral artery insertion by utilization of a surgical cut, because of the membrane thickness thereof, cannot be sufficiently wrapped or folded for percutaneous insertion. This would be the case even were a tapered balloon, as in Jones, used in that the membrane thickness at the wider diameter end portion of the balloon would, when folded or wrapped, present a substantial and unmanageable diametric bulk, even assuming the tapered end length is sufficiently collapsible. With regard to the thin membrane balloons, which incidentally are of only approximately one-half the membrane thickness of the earlier balloons as exemplified by Jones, there has been no successful resolution of the problem of abrasion and the rupturing resulting therefrom.

SUMMARY OF THE INVENTION

As little can be done about the increasing incidence of calcification in the lower aorta, in most instances occurring as a nature incident of an aging population, the problem of balloon rupture must be addressed by improvements in the construction of the balloon itself. To this end, the present invention proposes a balloon which is specifically adapted for percutaneous insertion, and which at the same time is highly resistant, and substantially impervious to abrasion induced rupture. As such, the invention eliminates the only practical problem remaining with the preferred percutaneous insertion technique.

Basically, the balloon of the invention is tapered to approximate the tapering of the descending aorta from its maximum diameter in the area of the highest blood flow at the aortic arch to its smallest diameter at the bifurcation of the femoral arteries. It is in the area of femoral arteries and the renal arteries thereabove where the calcified plaque is the greatest and where, with a conventional cylindrical balloon, the major abrasion occurs.

This tapering of the balloon is significant in that there is a reduction in the frequency and force of contact between the balloon and the aortic wall in this narrower critical area. A more important aspect of the taper is that the reduced diameter balloon allows for an increase in the wall or membrane thickness, again in this critical area, without increasing the cross-sectional area of the wrapped balloon to the point wherein percutaneous insertion through a sheath/dilator assembly would not be possible. In other words, the balloon of the invention is a thin membrane balloon which is thickened only within the tapered length toward one end thereof whereby the overall wrapped cross section of the tapered section is no greater than that of the larger diameter thin membrane portion of the balloon. It is only by this unique combination of a tapered end length for positioning toward the renal arteries, and a thickening of the membrane within this tapered area, preferably a progressive thickening as the balloon narrows, which provides, in a balloon catheter for percutaneous insertion, a substantial reduction in the incidence of abrasion related ruptures.

As an example, the catheter of the invention, assuming an approximate inflated volume of 40 cc, can be approximately 10–11½ inches long with the tapered length extending approximately ⅓ or more of this length inward from one end. The remainder of the length of the balloon can be cylindrical. Variations are possible, including the taper extending the full length of the balloon.

The section of the balloon of greatest internal diameter will be approximately 0.72 to 0.62 inches in diameter, thus slightly greater than the earlier known full length cylindrical balloon of approximately 0.57 inches. The internal balloon diameter at the end of the tapered section can be approximately 0.40 to 0.36 inches. The taper itself will normally be constant and at an angle of approximately one degree to two degrees.

Membrane or wall thickness at the greatest diameter will be from 0.0045 to a maximum of 0.0055 inches for a diameter increase of a maximum of 0.011 inches. At the taper end, the wall thickness will have an approximate maximum of 0.0065 inches, for a diameter increase of 0.013 inches.

These together with additional features and advantages of the invention will become more apparent from the detailed description of the invention following hereinafter.

BRIEF DESCRIPTION OF THE DRAWINGS

FIG. 1 is a schematic view illustrating the environmental positioning of the intra-aortic balloon catheter of the invention within the descending aorta;

FIG. 2 is a view of the balloon with portions broken away for purposes of illustration; and FIG. 3 is a similar elevational view of a variation of the balloon.

DESCRIPTION OF PREFERRED EMBODIMENTS

Referring now more specifically to the drawings, the intra-aortic balloon catheter 10, in FIG. 1, is schematically illustrated in its operative position within the descending aorta 12. The balloon 14 is of conventional material which can be described as flexible, flaccid and compliant, and preferably non-elastic or non-stretchable. The balloon, also in the manner of a conventional balloon, is adapted to be positioned with the distal balloon end 18 below the aortic arch 20 and the left subclavian artery 22. The proximal end 24 is to be positioned above the femoral arteries 26 and renal arteries 28 thereabove.

The descending aorta tapers or downwardly narrows from the aortic arch 22 to the renal arteries 28. The tapered lowered portion of the aorta, particularly in older patients, tends to become further restricted by the buildup of calcified atherosclerotic plaque and calcified lesions 29. It is this buildup in particular which has been found to excessive abrade the conventional cylindrical thin membrane balloon utilized in percutaneous insertion devices wherein the wrapped or folded balloon is inserted into the femoral artery through a tubular system referred to as a sheath/dilator assembly. This excessive abrasion in turn results in a rate of balloon rupture which is disturbing, particularly when considering the possible life-threatening effects thereof.

The present invention involves a two-part modification of the conventional balloon which substantially reduces or eliminates the incidence of abrasion-related rupture, while at the same time maintaining the collapsed bulk of the balloon at a minimum for use of the new balloon in the now universally accepted percutaneous insertion technique.

The balloon 14 of the present invention, when inflated, is configured to accommodate the natural tapering of the aorta 12, and as such, is narrower toward the proximal end 24 thereof for accommodation within the narrower portion of the aorta proximate the renal arteries. This narrowing of the balloon 14 comprises a tapering of the lower or proximal section 30 of the balloon 14. This tapered section, noting FIGS. 1 and 2, will be elongate, of a substantial length and normally extend approximately one-third to one-half or more of the length of the balloon 14. As suggested in the variation of FIG. 3, the taper may extend the full length of the balloon from proximal to distal end. The taper will be constant and, depending upon the relative length thereof, will be approximately at one degree to two degrees to the long axis of the balloon. The maximum internal diameter of the inflated balloon, whether this be along an elongate cylindrical distal length or section 32 of the balloon 14, as in FIGS. 1 and 2, or at the distal end 34, as in FIG. 3, will be approximately 0.72 to 0.62 inches. At the proximal end, the balloon will be approximately 0.40 to 0.36 inches. It is to be appreciated that these references to distal and proximal end diameters are at those points immediately inward of the sharply tapered end conical portions 36 and 38 wherein the balloon membrane is configured to engage and seal to the catheter 16.

The above described tapering of the balloon 14 allows, relative to the conventional cylindrical percutaneous insertion balloon, a relatively greater diameter at the wider portion of the balloon in that this greater diameter occurs only in the upper greater diameter section of the aorta. This in turn allows for a maintaining of the preferred balloon volume within the preferred length of approximately 10 to 11½ inches.

The tapered or narrower section or length 30 of the balloon 14, particularly closer to the proximal end of the balloon, is substantially narrower than the conventional catheter, 0.40 to 0.36 inches, as compared to 0.57 inches. As such, the tendency for abrasive engagement against the calcified plaque or lesions is substantially reduced. However, this in itself does not provide the balloon integrity considered necessary. Nevertheless, the tapered configuration is essential in order to enable incorporation of an important further improvement feature while still retaining the capability of use of the balloon in a percutaneous insertion technique.

The second significant feature of the invention is the specific thickening of the wall or membrane of the balloon in the section or tapered length of reduced diameter toward the proximal end of the balloon, and thus in the area of greatest calcification buildup and abrasion danger. The tapering allows for this increase in thickness, shown at a slightly exaggerated scale for purposes of illustration in FIGS. 2 and 3, in that the overall diameter or bulk of the wrapped balloon remains sufficiently compact as to allow for percutaneous insertion. Basically, the area of greatest membrane thickness corresponds to the area of minimal balloon diameter with the relationship therebetween being such as to maintain the desired compactness of the wrapped balloon. This also corresponds to the area of greatest balloon abrasion stress and the area within which, in the conventional catheter, rupture normally occurs. Without the narrowing or tapering of the proximal section of the catheter balloon, it would not be possible to provide the necessary membrane thickness and retain the ability for percutaneous insertion.

As an example of the membrane thicknesses involved, the membrane at its thinnest, in the elongate section 32 of the catheter of FIGS. 1 and 2, or along a generally equivalent length in the continuously tapering balloon of FIG. 3, can be on the order of 0.0045 to 0.0055 inches, and in the tapering or remaining section, generally uniformly increasing in thickness through an intermediate portion of a maximum of 0.0060 inches to the thickest portion adjacent the proximal end of 0.0065 inches. Thus, the external diameter adjacent or toward the distal end is approximately 0.009 to 0.011 inches greater than the internal diameter while the tapered length adjacent the proximal end has an external diameter approximately 0.013 inches greater than the internal diameter.

From the foregoing, it is to be recognized that the invention constitutes a unique solution to a significant problem within a specific area of technology. In accord therewith, the invention involves significant improvements within a catheter balloon particularly adapted for insertion into the aorta utilizing a percutaneous insertion technique. The improvements are specifically directed to the prevention of the major problem of abrasion-caused rupture of the balloon, a problem particularly derived from the necessity for the provision of a thin walled balloon which can be effectively collapsed and wrapped for percutaneous insertion.

In accord with the present invention, the problem of abrasive-induced rupture is solved or reduced to an acceptable level by modifying the balloon in two particulars, the tapering of the balloon to reduce engagement with the aorta wall toward the narrower portion of the aorta, and a simultaneous thickening of the balloon membrane within the tapered area.

The foregoing is considered illustrative of the invention, and the specifically described embodiments are not to be considered as limitations on the scope of the invention. Rather, the invention is only to be limited by the scope of the claims following hereinafter.

I claim:

1. An intra-aortic balloon catheter assembly for accommodation within an aorta generally tapering between a maximum cross-sectional area adjacent the aortic arch and a generally smaller cross-sectional area adjacent renal arteries spaced from the aortic arch; the balloon catheter assembly being adapted for enhanced resistance to failure from abrasive calcification deposits within the aorta in the vicinity of the renal arteries, said balloon catheter assembly comprising an elongate catheter and an elongate balloon mounted to the catheter, said balloon having opposed first and second end portions, and comprising an inflatable flexible membrane said balloon being inflatable and having an inflated configuration comprising a first elongate section of predetermine length extending inward from said first end portion of said balloon and adapted to be positioned within the aorta to extend inwardly from the smaller cross-sectional area of the aorta toward the aortic arch, said inflated balloon between said first elongate section and said second end portion defining a second section, said first elongate section, along the length thereof, having a smaller cross-sectional area than said second section of said inflated balloon, said second section having a predetermined membrane thickness, said first section having a membrane thickness greater than the membrane thickness of said second section.

2. In the balloon catheter assembly of claim 1, said membrane thickness in said first section progressively increasing in thickness from said second section to said first end portion of said balloon.

3. In the balloon catheter assembly of claim 2, said membrane thickness in said second section being constant.

4. In the balloon catheter assembly of claim 3, said first section having of a tapered configuration, tapering progressively from said second section to the smallest cross-sectional area adjacent said first end portion of said inflated balloon.

5. In the balloon catheter assembly of claim 4, said tapered configuration of said first section continuing from said first section along said second section toward said second end portion with increasingly greater cross-sectional areas.

6. In the balloon catheter assembly of claim 4, said second section of said inflated balloon being of a constant cross-section throughout the length thereof.

7. In the balloon catheter assembly of claim 2, said first section having a tapered configuration, tapering progressively from said second section to the smallest cross-sectional area adjacent said first end portion of said inflated balloon.

8. In the balloon catheter assembly of claim 7, said tapered configuration of said first section continuing from said first section along said second section toward said second end portion with increasingly greater cross-sectional areas.

9. In the balloon catheter assembly of claim 7, said second section of said inflated balloon being of a constant cross-section throughout the length thereof.

10. In the balloon catheter assembly of claim 1, said t membrane thickness in said second section being constant.

11. In the balloon catheter assembly of claim 10, said first section having of a tapered configuration, tapering progressively from said second section to the smallest cross-sectional area adjacent said first end portion of said inflated balloon.

12. In the balloon catheter assembly of claim 1, said first section having of a tapered configuration, tapering progressively from said second section to the smallest cross-sectional area adjacent said first end portion of said inflated balloon.

13. In the balloon catheter assembly of claim 12, said second section of said inflated balloon being of a constant cross-section throughout the length thereof.

14. In the balloon catheter assembly of claim 1, said second section of said inflated balloon being of a constant cross-section throughout the length thereof.

15. An intra-aortic balloon catheter assembly for pumping blood in a cardiac assist system, said balloon catheter assembly being adapted for accommodation within an aorta having a tapered configuration from the aortic arch to a narrow portion proximate associated renal arteries, said aorta being susceptible to internal calcification build-up; the balloon catheter assembly being adapted for enhanced resistance to abrasive effect of the internal calcification build-up particularly adjacent the renal arteries, said balloon catheter assembly comprising a catheter having a closed leading end and a following end, and an elongate inflatable and deflatable catheter balloon surrounding said catheter, said balloon comprising a flaccid membrane having a distal end sealed to the catheter adjacent the leading end thereof and a proximal end sealed to the catheter inward of the leading end, said balloon, when inflated, having a tapered linear section thereof, extending inward from said proximal end towards said distal end, said balloon having an increasing cross-section for general conformance to and generally uniform accommodation within the tapering configuration of the aorta from the renal arteries toward the aortic arch, said balloon membrane having a predetermined thickness adjacent said distal end and an increased thickness at and immediately adjacent the proximal end for enhanced resistance to abrasion within the narrower portion of the aorta.

16. In the catheter assembly of claim 15, said tapered linear section being elongate, and said balloon further comprises a second constant diameter section being of a length extending between said tapered section and said distal end, said second constant diameter section having said predetermined membrane thickness throughout the length of said second constant diameter section.

17. In the catheter assembly of claim 15, said inflated balloon has a length between the proximal and the distal end of the membrane, said balloon tapering throughout the length of the balloon with progressively increasing cross-sectional areas from the proximal end to the distal end.

18. In the aortic pump of claim 17, said membrane, for a length inward thereof from the distal end, being of said predetermined thickness.

19. An inflatable catheter balloon adapted for percutaneous insertion within a tapering interior of an aorta, said balloon being of an elongate configuration and including opposed first and second end portions, said balloon comprising an impermeable membrane having, a thickness greater toward said first end portion of said balloon than toward said second end portion thereof, said balloon, when inflated, being of a lesser cross-sectional area toward said first end portion thereof than toward said second end portion, wherein said balloon generally conforms to the tapering interior of the aorta and is of greater resistance to abrasion toward said first end portion of said balloon.

20. A method of positioning an inflatable catheter balloon in an aorta having an aortic arch and a naturally occurring narrowing section comprising the steps of:

(a) forming a balloon having an elongate configuration, opposed first and second end portions, greater balloon wall thickness toward said first end portion and, when inflated, a lesser cross-sectional area toward said first end portion;

(b) closely wrapping the deflated balloon about an associated catheter;

(c) percutaneously inserting the catheter and wrapped balloon into an artery leading to the aorta;

(d) directing the balloon into the aorta; and (e) positioning the balloon lengthwise in the aorta between the aortic arch and renal arteries therebelow with the thickened first end portion of the balloon of lesser cross-sectional area being directed toward the renal arteries and the naturally occurring narrowering section of the aorta.

* * * * *